United States Patent [19]
Jia

[11] Patent Number: 5,770,788
[45] Date of Patent: Jun. 23, 1998

[54] INDUCING CHROMOSOME DOUBLING IN ANTHER CULTURE IN MAIZE

[76] Inventor: Xu Jia, Institute of Genetics, Academia Sinica, Beijing, China

[21] Appl. No.: 469,794

[22] Filed: Jun. 6, 1995

Related U.S. Application Data

[63] Continuation of Ser. No. 251,655, May 31, 1994, abandoned, which is a continuation of Ser. No. 689,175, Apr. 23, 1991, abandoned.

[30] Foreign Application Priority Data

Apr. 23, 1990 [GB] United Kingdom ................ 9009090.3

[51] Int. Cl.$^6$ .......................... C12N 15/00; C12N 15/29; A01H 4/00; A01H 5/00
[52] U.S. Cl. ................................. 800/200; 800/DIG. 56; 435/418; 435/419; 435/424; 435/430; 514/629; 47/58
[58] Field of Search ........................... 800/200, DIG. 56; 435/240.4, 240.45, 240.46, 240.48, 240.49, 240.5, 240.54, 419, 418, 424, 430; 514/629; 47/58

[56] References Cited

PUBLICATIONS

Wan et al., Thoer. Appl. Genet., 81:205–211, 1991.
Murashige, T., Skoog, F. (1962) A Revised medium for Rapid Growth and Bioassays with Tobacco Tissue Cultures. Physiol. Plant 15:473–497.
Jensen, C. J. (1974) Chromosome Doubling Techniques in Haploids, In: Kasha, K. J. (ed.) Haploids in Higher Plants: Advances and Potentials. Univ. Press, Guelph, pp. 153–190.
Anonymous, 401 Research Group (1975) Primary Study on Induction of Pollen Plants of Zea mays (English Abstract) Acta. Genetc. Sin. 2:143.
Sunderland, N. (1979) Anther and Pollen Culture 1974–1979, pp. 171–183 in The Plant Genome and 2nd Int. Haploid Conference. John Innes Symp.
Miao, S. H. (1980) Effect of Different Ammonium Salts on the Formation of Maize Pollen Embryoids. Acta. Bot. Sin. 22:356–359.
Brettell, R. I. S., et al., (1981) Production of Haploid Maize Plants by Anther Culture. Maydica 26:101–111.
Chu, C. C. (1981) The N6 Medium nd Its Applications to Anther Culture of Cereal Crops. Proc. Symp. Plant tissue culture, Beijing 1978. Pitman, Boston, pp. 43–50.
Ku, M. K., Cheng, W. C., et al., (1981) Induction Factors and Morphocytological Characteristics of Pollen–Derived Plants in Maize (Zea Mays). Proc. Symp. Plant Tissue Culture, Beijing 1978. Pitman, Boston, pp. 35–42.
Miao, S. H., Kuo, C. S., et al. (1981) Induction of Pollen Plants of Maize and Observations on Their Progeny. Proc. Symp. Plant tissue culture, Beijing 1978. Pitman, Boston, pp. 23–34.
Ting, Y. C., Yu, M., et al. (1981) Improved Anther Culture of Maize (Zea mays). Plant Sci. Lett. 23:139–145.

Genovesi, A. D. et al., (1982) In Vitro Production of Haploid Plants of Corn via Anther Culture, Crop Sci 22:1137–1144.
Kuo, C. S., et al. (1985) Corn (Zea mays L.): Production of Pure Lines Through Anther Culture, In: Bajaj, YPS (ed.) Biotechnology in Agriculture and Forestry, v. 2, Cross I, Springer, N.Y. pp. 152–164.
Duncan, D. R., Williams, M. E., et al., (1985) The Production of Callus Capable of Plant Regeneration from Immature Embryos of Numerous Zea mays Genotypes. Planta 165:322–332.
Pauk, J. (1985) Production of Haploid Plants of Maize (Zea mays L.) Through Androgenesis. Cereal Res. Commun. 13:47–53.
Wei, Z. M. et al. (1986) Callus Formation and Plant Regeneration Through Direct Culture of Isolated Pollen of Hordeum vulgare cv. 'Sabarlis', Theor. Appl. Genet. 72:252–255.
Sorvari, S., (1986) The Effect of Starch Gelatinized Nutrient Media in Barley Anther Cultures, Ann. Agric. Fenn. 25:127–133.
Sorvari, S., (1986) Comparison of Anther Cultures of Barley Cultivars in Barley–Starch and Agar Gelatinized media, Ann. Agric. Fenn. 25:249–254.
Dieu, P., Becker, M. (1986) Further Studies of Androgenetic Embryo Production and Plant Regeneration from in vitro Cultured Anthers in Maize (Zea mays L.). Maydica 31:245–259.
Petolino, J. F., Jones, A. M., (1986) Anther Culture of Elite Genotypes of Zea mays L. Crop Sci., 26:1027–1074.
Olsen, F. (1987) Induction of Microspore Embryogenesis in Cultured Anthers of Hordeum Vulgare. The Effects of Ammonium Nitrate, Glutamine and Asparagine as Nitrogen Sources, Carlesberg Res. Commun. 52:393–404.
Petolino, J. F., et al. (1987) Genetic Analysis of Anther Culture Response in Maize, Theor. Appl. Genet. 74:284–286.
Keller, W. A., et al. (1987) Haploids from Gametophytic Cells–Recent Developments and Future Prospects, Plant Tiss. and Cell Cul., Alan R. Liss, Inc., pp. 223–241. Close, K. R., Ludeman, L. A. (1987) The Effect of Auxin–Like Plant Growth Regulators and Osmotic Regulation on Induction of Somatic Embryogenesis from Elite Maize Inbreds. Plant Sci. 52:81–89.
Nitsch, C., Andersen, S., et al., (1987) Production of Haploid Plants of Zea mays and Pennisetum Through Androgenesis.

(List continued on next page.)

Primary Examiner—Douglas W. Robinson
Assistant Examiner—Thomas Haas

[57] ABSTRACT

Fertile corn plants are produced by culturing anthers or pollen in the presence colchicine which is added to an otherwise ordinary anther culture medium after a pre-culture phase in the absence of the colchicine. The colchicine induces doubling of the chromosome numbers in regenerated plants which would otherwise be infertile haploids. Haploid doubling provides a rapid route to homozygous parental plant lines.

1 Claim, No Drawings

OTHER PUBLICATIONS

In: Earle E. D., Demarly Y. (eds) Variability in Plants Regenerated from Tissue Culture. Praeger, N.Y., pp. 69–91.

Pace, G. M., Reed, J. N., et al. (1987) Anther Culture of Maize and the Visualization of Embryogenic Microspores by Fluorescent Microscopy. Theor. Appl. Genet. 73:863–869.

Sletten, M. C., Tomes, D. F., (1987) Plant Recovery from Type I and Type II. Embryogenic Callus in Maize. In Vitro 23:26A.

Hunter, et al., 91988) Maltose–The Preferred Carbon Source for Barley Anther Culture, Shell Research Limited.

Songstad, D. D., et al. (1988) Effect of 1–Aminocyclopropane–1–Carboxylic Acid, Silver Nitrate, and Norbornadiene on Plant Regeneratin from Maize Callus Cultures, Plant Cell Rep. 7:262–265.

Petolino, J. F., et al. (1988) Selection for Increased Anther Culture Response in Maize, Theor. Appl. Genet. 76:157–159.

Rhodes, C. A., Lowe, K. S., Ruby, K. L. (1988) Plant Regeneration from Protoplasts Isolated from Embryogenic Maize Cell Cultures. Biotechnology 6:56–60.

Wan, Y., et al. (1989) Efficient Production of Doubled Haploid Plants Through Colchicine Treatment of Anther–Derived Maize Cells, Theor. Appl. Genet. 7:889–892.

Pescitelli, S. M., et al. (1989) High Frequency Androgenesis from Isolated Microspores of Maize, Plant Cell Rep. 7:673–676.

Coumans, M. P., et al., (1989) Plant Development from Isolated Microspores of *Zea mays* L., Plant Cell Rep. 7:618–621.

Vain, P., et al., (1989) Enhancement of Production and Regeneration of Embryogenic Type II Callus in *Zea mays* L. by AgNO3, Plant Cell. Tissue and Organ Culture 18:143–151.

Personal Communication, Finn Dok to Dennis Genovesi (1989).

Genovesi, A. D. (1990) Maize (*Zea mays* L.): In Vitro Production of Haploids.

Pescitelli, S. M., et al. (1990) Isolated Microspore Culture of Maize: Effects of Isolation Technique, Reduced Temperature, and Sucrose Level, Plant Cell Rep. 8:628–631.

Sigma ad, Membrane Rafts, (1990).

Roberts–Oehlschlager, S. L., Dunwell, J. M. Faulks, R. (1990) Changes in the Sugar Content of Barley Anthers During Culture on Different Carbohydrates. Plant Cell. Tissue and Organ Culture 22:77–85.

Pescitelli et al (1989) Plant Cell Reports 7:673–676.

Pace et al (1987) Theor Appl Genet 73:863–869.

Sigma Catalog (Spring 1990).

Cheng et al (16 May 1977) Science 198:306–307.

Sorvari (1986) Annales Agricultural Fenniae 25: 127–133, Seria Agricultura N. 76.

Wei et al (1986) Theor Appl Senet. 72:252–255.

Roberts–Oehlschlager et al (1990) Plant Cell Tissue & Orgen Culture 22: 77–85.

Huang Jiaoxiang, Guam Yuelam & Zheng Wanzhem, 1981: Effects of Colchicine on Ploidy Level of Anther Culture in Maize Ann. Report of the Institute of Genetics. Acad. Sinica 1980.

"Maize: In Vitro Production of Haploids"; Genovesi, N. in Biotechnology in Agriculture & Forestry, 12 (1990).

Jiaoxiang et al. 1981, In 1980 Annual Report of the Institute of Genetics Academia Sinica. pp. 101–102.

Jensen, C.J. Chromosome Doubling Techniques in Haploids. 1974. in Haploids in Higher Plants, Proceedings of the Irst. International Symposium. ed. Kasha. Univ. of Guelph Press, Ontario.

Nitsch, C. Z. Culture of Isolated Microspores. 1977. in Plant Cell Tissue, and Organ Culture. ed. J. Reinert & Y.P.S. Bajaj. Springer–Verlag.

Sunderland, N. & J. M. Dunwell. 1977. Anther and Pollen Culture in Plant Tissue and Cell Culture. ed. H.E. Street. Blackwell Scientific Publications.

Wan, Y., J.F. Petolino, and J.M. Widholm. 1989. Efficient Production of Doubled Haploid Plants Through Colchicine Treatment of Anther–Derived Maize Callus. Theor. Appl. Genet. 77: 889–892.

Nitsch, C., S. Anderson, M. Godard, M.G. Neuffer, & W.F. Sheridan. 1982. Production of Haploid Plants of *Zea mays* and *Pennisetum* through Androgenesis. in Variability in Plants Regenerated from Tissue Culture. ed. E. D. Earle & Yves Demarly.

Petolino, J.F. and A.M. Jones. 1986. Anther Culture of Elite Genotypes of Maize. Crop Science, 26: 1072–1074.

INDUCING CHROMOSOME DOUBLING IN ANTHER CULTURE IN MAIZE

This is a continuation of application Ser. No. 08/251,655 filed on May 31, 1994, now abandoned, which is a continuation of Ser. No. 07/689,175, filed Apr. 23,1991, now abandoned, This invention relates to a method of producing plants. More specifically the invention relates to a method of producing corn (*Zea mays*) plants for use as breeding stock in a plant breeding programme.

BACKGROUND OF THE INVENTION

Plant breeding comprises screening potential parental varieties for desirable characteristics and crossing selected parental lines to introduce those desirable characteristics into the progeny of the cross. One difficulty encountered by breeders is that, in the act of crossing, not only the desirable trait is transferred to the progeny but a a certain amount of randomization of the genomes of both parental lines occurs leading to a wide variety of morphology and other features of the progeny. This makes selection of the desired progeny difficult, particularly if expression of the desired trait is not visually obvious as this would necessitate laboratory analysis of the whole progeny generation. Detection of a genetically recessive trait is particularly difficult.

To overcome this difficulty, breeders tend to work with homozygous parental lines (inbreds) so that the genetic make up of the F1 generation is more predictable. When a desirable trait is detected in a heterozyote, breeders have to subject the plant to a succession of back-crosses with its parent lines, followed by selection and further back-crossing. Eventually a plant is derived which is homozygous in the desired trait. Of course, the time scale involved here is dictated by the rate at which plants grow to maturity and set seed and several years can be necessary to produce the desired homozygous parent line.

Haploid plants contain only one half of the usual complement of genes. Such plants are capable of growing to maturity but are sterile. There are several known methods of generating haploids in corn. Plants are known which possess an indeterminate gametophyte (ig) gene and there is also a line known as Stock 6 which has a similar propensity to generate haploids. Utilization of either ig or Stock 6 in a cross will result in some haploid plants in the progeny. Another method is to regenerate whole plants from pollen cells which are haploid. AS plants develop gametes, pollen, for example, the cells involved undergo meiosis which is a process during which the cells divide into daughter cells which each contain only one half of the complement of chromosomes of the plant. Normal plants are diploid, that is they have two complete sets of chromosomes, one from each parent. Polyploid plants which have greater numbers of sets of chromosomes are also known.

Corn plants can be stimulated to divide to produce embryos and, ultimately, plants. Ninety percent of these plants, being haploid, fail to produce seed. In 10% of cases (on average) spontaneous doubling occurs at some point during pollen culture and plant regeneration and a fertile doubled haploid is produced. Doubled haploids offer the quickest possible approach to homozygosity (pure lines). It is believed that one to two years can be saved in the testing phase of a corn breeding programme through the use of doubled haploids.

Recovery of plants from cultured pollen/anthers of corn is at present a low frequency event and is only possible from a small number of genotypes. The usefulness of the process to plant breeders would be improved if (a) more plants could be produced from pollen grains of a wide range of genotypes, and, (b) the percentage of plants setting seed could be increased. The present invention addresses (b).

An object of the present invention is to provide an improved method for the production of plants.

SUMMARY OF THE INVENTION

According to the present invention there is provided a method for the production of plants, comprising culturing anthers or pollen of the target plant in a culture medium containing an effective amount of a chemical agent capable of inducing chromosome multiplication in haploid cells.

According to the present invention there is provided also a method for the production of fertile corn plants, comprising culturing anthers or pollen of *Zea mays* in a culture medium containing an effective amount of a chemical agent capable of inducing chromosome multiplication in haploid cells and regenerating and recovering fertile diploid plants from the culture.

Preferably the chemical agent is colchicine or an analogue thereof.

Preferably an ordinary anther culture be established and allowed to establish for a period of time (from about seven to fourteen days, usually about ten days is sufficient for maize) before the colchicine is added to the medium.

Thus, our invention is based on our discovery that there is a particular stage in microspore-derived embryo development, which occurs at around seven to fourteen days after microspore or anther culture initiation, during which chemical agents capable of inducing chromosome multiplication is most effective. Application of the agent at this developmental stage results in an increased proportion of plants being diploid and fertile, compared with application at other stages.

The invention will now be described, by way of illustration, by the following Example.

EXAMPLE

A sample of 9052 anthers, bearing pollen at the mid-to late uninucleate stage, were dissected from florets of field-grown hybrid corn (FH24×AP81). The anthers were placed in a liquid medium containing N6 salts in an 8 ml, 60 mm diameter petri dish. The medium composition was as follows:

| | |
|---|---|
| 2,4-dichlorophenoxyacetic acid | 2 mg/ml |
| kinetin | 1 mg/ml |
| BAP | 1 mg/ml |
| casein hydrolysate | 500 mg/ml |
| sucrose | 12% |
| activated charcoal | 0.5% |
| pH (adjusted with potassium hydroxide/hydrochloric acid) | 5.8 |

After ten days 2ml of colchicine, in medium having the composition described above, were added to the medium to give a final volume of 10 ml containing 50 ppm of colchicine. After a further three days the anthers were removed from the medium and placed on an agar-solidified (0.6%) medium of the same composition but without colchicine.

As a control 8889 anthers were cultured identically but without the addition of the colchicine after ten days.

After between 40 and 60 days incubation, pollen embryos which had emerged from the cultured anthers were transferred to an N6 medium containing no 2,4-D, 1.5 mg/ml kinetin and 5% sucrose. On this medium the pollen embryos continued to develop, eventually germinating to produce plantlets. Following germination, plantlets were transferred to an N6-based medium containing 0.03 mg/ml NAA, 2.0 mg/ml kinetin and 3% sucrose to promote further growth and root production.

Plants with a well-established root system were transferred to soil and grown to maturity in a greenhouse.

The results are shown in the Table below.

TABLE

| Colchicine Treatment | 0 ppm | 50 ppm |
|---|---|---|
| No. of anthers plated | 8889 | 9052 |
| No. of pollen embryos | 98 | 89 |
| No. of plants | 21(10)* | 22 |
| No. of plants setting seed | (3)* | 18 |

*From 8889 anthers planted and cultured in the absence of colchicine, 21 plants in all were produced. Of these, eleven were used in another experiment and of the remaining 10, only three set seed (30%). In the presence of 50 ppm colchicine, the relative proportion of plants recovered was of the same order as the control but the proportion of these which were able to set seed was increased by a factor of, roughly, three.

These results, which were reproduced several times, show, therefore, that (a) the colchicine treatment has no deleterious effects on the frequency of plant production since the numbers of plants produced under treatment conditions is roughly the same as under control (zero colchicine) treatment, and, (b) culture in the presence of colchicine at 50 ppm for three days after culture for 10 days in liquid medium increases the percentage of plants capable of setting seed from 30% to 82%.

The progeny of the plants obtained by this method have been shown to be homozygous (doubled haploids) by isozyme analysis and field observation.

What is claimed is:

1. A method for the production of fertile corn plants, comprising culturing anthers or microspores of *Zea mays* in a culture medium for seven to fourteen days, adding to the medium at a concentration of at least 50 ppm of colchicine to induce chromosome doubling in microspores, allowing said colchicine to act upon the cultured microspores, removing the microspores from said medium and said colchicine within three days and thereafter regenerating fertile doubled haploid plants from the cultured microspores.

* * * * *